United States Patent [19]

Pearson et al.

[11] Patent Number: 5,919,952
[45] Date of Patent: Jul. 6, 1999

[54] METHOD FOR PREPARING SWAINSONINE

[75] Inventors: William H. Pearson; Erik J. Hembre, both of Ann Arbor, Mich.

[73] Assignee: The Regents of the University of Michigan, Ann Arbor, Mich.

[21] Appl. No.: 08/943,693

[22] Filed: Oct. 3, 1997

Related U.S. Application Data

[60] Provisional application No. 60/027,807, Oct. 4, 1996.

[51] Int. Cl.$^6$ .......................... C07F 7/02; C07D 221/02; C07D 317/18
[52] U.S. Cl. .......................... 549/214; 549/320; 546/183
[58] Field of Search .................................. 549/214, 320; 546/183

[56] References Cited

U.S. PATENT DOCUMENTS

| | | | |
|---|---|---|---|
| 5,023,340 | 6/1991 | Fleet | 548/453 |
| 5,187,279 | 2/1993 | Cha et al. | 546/183 |
| 5,376,452 | 12/1994 | Hope et al. | 428/402.2 |

FOREIGN PATENT DOCUMENTS 61-277685  12/1986  Japan .

OTHER PUBLICATIONS

Pearson et al, *J. Org. Chem.*, vol. 57, pp. 3977–3987 (1992).
Pearson et al, *Tetrahedron Lett.*, vol. 32, pp. 5513–5516 (1991).
Pearson et al, *Tetrahedron Lett.*, vol. 34, pp. 8221–8224 (1993).
Pearson et al, *J. Org. Chem.*, vol. 61, pp. 5537–5545, 5546–5556 (1996).
Guengerich et al, *J. Am. Chem. Soc.*, vol. 95, pp. 2055–2056 (1973).
Schneider et al, *Tetrahedron*, vol. 39, pp. 29–32 (1983).
Hino et al, *J. Antibiot.*, vol. 38, pp. 926–935 (1985).
Patrick et al, *Biotechnol. Lett.*, vol. 17, pp. 433–438 (1995).
Colegate et al, *Aust. J. Chem.*, vol. 32, pp. 2257–2264 (1979).
Molyneux et al, *Science*, vol. 216, pp. 190–191 (1982).
Molyneux et al, *J. Nat. Prod.*, vol. 58, pp. 878–886 (1995).
Nishimura, in *Studies in Natural Products Chemistry*, Atta–ur–Rahman, Ed., Elsevier: Amsterdam, vol. 10, pp. 495–583 (1992).
Elbein, *Ann. Rev. Biochem.*, vol. 56, pp. 497–534 (1987).
Cenci di Bello et al, *Biochem. J.*, vol. 259, pp. 855–861 (1989).
Winchester et al, *Glycobiology*, vol. 2, pp. 199–210 (1992).
Kaushal et al, *Methods in Enzymology*, vol. 230, pp. 316–329 (1994).
Goss et al, *Clin. Cancer Res.*, vol. 1, pp. 935–944 (1995).
Das et al, *Oncol. Res.*, vol. 7, pp. 425–433 (1995).
Suami et al, *Chem. Lett.*, pp. 513–516 (1984).
Ali et al, *J. Chem. Soc., Chem. Commun.*, pp. 447–448 (1984).
Fleet et al, *Tetrahedron Lett.*, vol. 25, pp. 1853–1856 (1984).
Yasuda et al, *Chem. Lett.*, pp. 1201–1204 (1984).

Adams et al, *J. Org. Chem.*, vol. 50, pp. 420–422 (1985).
Suami et al, *Carbohydr. Res.*, vol. 136, pp. 67–75 (1985).
Setoi et al, *J. Org. Chem.*, vol. 50, pp. 3948–3950 (1985).
Ali et al, *Carbohydr. Res.*, vol. 136, 225–240 (1985).
Ikota et al, *Chem. Pharm. Bull.*, vol. 35, pp. 2140–2143 (1987).
Ikota et al, *Heterocycles*, vol. 26, pp. 2369–2370 (1987).
Bashyal et al, *Tetrahedron*, vol. 43, pp. 3083–3093 (1987).
Dener et al, *J. Org. Chem.*, vol. 53, pp. 6022–6030 (1988).
Carpenter et al, *Tetrahedron Lett.*, vol. 30, pp. 7261–7264 (1989).
Bennett et al, *J. Am. Chem. Soc.*, vol. 111, pp. 2580–2582 (1989).

(List continued on next page.)

*Primary Examiner*—Amelia Owens
*Attorney, Agent, or Firm*—Oblon, Spivak, McClelland, Maier & Neustadt, P.C.

[57] ABSTRACT

(–)-Swainsonine may be prepared by (i) reacting a compound of formula (8):

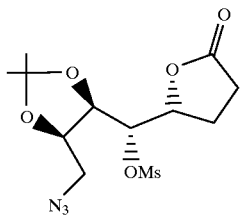

(8)

wherein OMs is methanesulfonyl with $H_2$ in the presence of $Pd(OH)_2$ followed by NaOMe, to obtain a compound of formula (9):

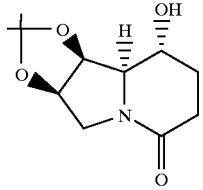

(9)

and (ii) reducing the carbonyl group and hydrolyzing the ketal group in the compound of formula (9) to obtain (–)-swainsonine of formula (1):

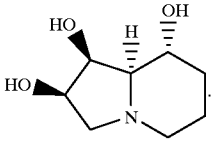

(1)

14 Claims, No Drawings

OTHER PUBLICATIONS

Pearson et al, *Tetrahedron Lett.*, vol. 31, pp. 7571–7574 (1990).
Miller et al, *J. Am. Chem. Soc.*, vol. 112, pp. 8100–8112 (1990).
Ikota et al, *Chem. Pharm. Bull.*, vol. 38, pp. 2712–2718 (1990).
Naruse et al, *J. Org. Chem.*, vol. 59, pp. 1358–1364 (1994).
Hunt et al, *Tetrahedron Lett.*, vol. 36, pp. 501–504 (1995).
Kang et al, *Tetrahedron Lett.*, vol. 36, pp. 5049–5052 (1995).
Oishi et al, *Synlett*, pp. 404–406 (1995).
Gonzalez et al, *Bull. Chem. Soc. Jpn.*, vol. 65, pp. 567–574 (1992).
Honda et al, *J. Chem. Soc., Perkin Trans. 1*, pp. 2091–2101 (1994).
Angermann et al, *Synlett*, pp. 1014–1016 (1995).
Zhou et al, *Tetrahedron Lett.*, vol. 36, pp. 1291–1294 (1995).
Zhou et al, *Chem. Soc., Perkin Trans. 1*, pp. 2599–2604 (1995).
Kim et al, *Tetrahedron Lett.*, vol. 30, pp. 5721–5724 (1989).
Ina et al, *J. Org. Chem.*, vol. 58, pp. 52–61 (1993).
Jirousek et al, *Tetrahedron Lett.*, vol. 34, pp. 3671–3674 (1993).
Kim et al, *J. Org. Chem.*, vol. 58, pp. 7096–7099 (1993).
Poitout et al, *Tetrahedron Lett.*, vol. 35, pp. 3293–3296 (1994).
Lohray et al, *J. Org. Chem.*, vol. 60, pp. 5958–5960 (1995).
Cohen et al, *J. Am. Chem. Soc.*, vol. 105, pp. 3661–3672 (1983).
Cohen et al, in *Organic Syntheses*, Collective vol. VII, J. P. Freeman, Ed., Wiley: New York, pp. 297–301 (1990).
Dunigan et al, *J. Org. Chem.*, vol. 56, pp. 6225–6227 (1991).
Mekki et al, *Tetrahedron Lett.*, vol. 32, pp. 5143–5146 (1991).
Johnson et al, *J. Am. Chem. Soc.*, vol. 92, pp. 741–743 (1970).
Sharpless et al, *J. Org. Chem.*, vol. 57, pp. 2768–2771 (1992).
Wang et al, *Tetrahedron Lett.*, vol. 33, pp. 6407–6410 (1992).
Keinan et al, *Tetrahedron Lett.*, vol. 33, pp. 6411–6414 (1992).
Keck, *J. Org. Chem.*, vol. 58, pp. 6083–6089 (1993).
Still et al, *J. Org. Chem.*, vol. 43, pp. 2923–2925 (1978).
Pearson et al, *J. Org. Chem.*, vol. 56, pp. 1976–1978 (1991).

METHOD FOR PREPARING SWAINSONINE

This application claims priority to and incorporates U.S. Provisional Application Ser. No. 60/027,807 filed Oct. 4, 1996.

This work was funded by the National Institutes of Health (GM-35572) and was supported in part by National Research Service Award T32 GM07767. Thus, the United States Government may have some rights in this application.

BACKGROUND OF THE INVENTION

1. Field of the Invention

The present invention relates to a method for preparing swainsonine. The present invention also relates to novel intermediates useful for the production of swainsonine.

2. Discussion of the Background

The indolizidine alkaloid (−)-swainsonine (1) is of long standing interest due to its diverse biological activity. For the isolation from the fungus Rhizoctonia leguminicola, see:

(a) Guengerich, F. P.; DiMari, S. J.; Broquist, H. P. J. Am. Chem. Soc. 1973, 95, 2055.

(b) Schneider, M. J.; Ungemach, F. S.; Broquist, H. P.; Harris, T. M. Tetrahedron 1983, 39, 29–32.

For the isolation from the fungus Metarhizium anisopliae, see:

(c) Hino, M.; Nakayama, O.; Tsurumi, Y.; Adachi, K.; Shibata, T.; Terano, H.; Kohsaka, M.; Aoki, H.; Imanaka, H. J. Antibiot. 1985, 35, 926–935.

(d) Patrick, M. S.; Adlard, M. W.; Keshavarz, T. Biotechnol. Lett. 1995, 17, 433–438.

For the isolation from the legume Swainsona canescens, see:

(e) Colegate, S. M.; Dorling, P. R.; Huxtable, C. R. Aust. J. Chem. 1979, 32, 2257–64.

For the isolation from the locoweed Astragalus lentiginosus, see:

(f) Molyneux, R. J.; James, L. F. Science, 1982, 216, 190–191.

For the isolation from Weir vine, see:

(g) Molyneux, R. J.; McKenzie, R. A.; O'Sullivan, B. M.; Elbein, A. D. J. Nat. Prod. 1995, 58, 878–886.

For a review of the synthesis and biological activity of swainsonine and other glycosidase inhibitors, see: Nishimura, Y. In Studies in Natural Products Chemistry; Atta-ur-Rahman, Ed.; Elsevier: Amsterdam, 1992; Vol. 10; pp 495–583.

(−)-Swainsonine may be considered an azasugar analog of mannose, and is indeed a potent inhibitor of many mannosidases including the glycoprotein processing enzyme mannosidase II (see: Elbein, A. D. Ann. Rev. Biochem 1987, 56, 497–534; Cenci Di Bello, I.; et al Biochem. J. 1989, 259, 855–861; Winchester, B., et al; Glycobiology, 1992, 2, 199–210; and Kaushal, G. P.; Elbein, A. D. Methods in Enzymology 1994, 230, 316–329). Swainsonine is the first glycoprotein-processing inhibitor to be selected for clinical testing as an anticancer drug (see: Goss, P. E.; Baker, M. A.; Carver, J. P.; Dennis, J. W. Clin. Cancer Res. 1995, 1, 935–944; and Das, P. C.; Roberts, J. D.; White, S. L.; Olden, K. Oncol. Res. 1995, 7, 425–433), but its high cost has hindered clinical trials. For example, Sigma Chemical Co. currently sells 1 mg of (−)-swainsonine isolated from *Rhizoctonia leguminicola* for ca. $100 USD (1995 catalog). Toronto Research Chemicals currently sells 1 mg of synthetic (−)-swainsonine for ca. $40. Apparently, there is still no cost-effective way to either isolate swainsonine from natural sources or to prepare it synthetically.

A great deal of effort has been expended on developing synthetic routes to swainsonine. See e.g., (a) Suami, T.; Tadano, K.; Iimura, Y. Chem. Lett. 1984, 513–516.

(b) Ali, M. H.; Hough, L.; Richardson, A. C. J. Chem. Soc., Chem. Commun. 1984, 447–448.

(c) Fleet, G. W. J.; Gough, M. J.; Smith, P. W. Tetrahedron Lett. 1984, 25, 1853–1856.

(d) Yasuda, N.; Tsutsumi, H.; Takaya, T. Chem. Lett. 1984, 1201–1204.

(e) Adams, C. E.; Walker, F. J.; Sharpless, K. B. J. Org. Chem. 1985, 50, 420–422.

(f) Suami, T.; Tadano, K. Iimura, Y. Carbohydr. Res. 1985, 136, 67–75.

(g) Ali, M. H.; Hough, L. Richardson, A. C. Carbohydr. Res. 1985, 136, 225–240.

(h) Setoi, H.; Takeno, H.; Hashimoto, M. J. Org. Chem. 1985, 50, 3948–3950.

(i) Ikota, N.; Hanaki, A. Chem. Pharm. Bull. 1987, 35, 2140–21433.

(j) Ikota, N.; Hanaki, A. Heterocycles 1987, 26, 2368.

(k) Bashyal, B. P.; Fleet, G. W. J.; Gough, M. J.; Smith, P. W. Tetrahedron 1987, 43, 3083.

(l) Dener, J. M.; Hart, D. J. Ramesh, S. J. Org. Chem. 1988, 53, 6022–6030.

(m) Carpenter, N. M.; Fleet, G. W. J.; diBello, I. C.; Winchester, B.; Fellows, L. E.; Nash, R. J. Tetrahedron Lett. 1989, 30, 7261–7264.

(n) Bennett, R. B., III; Choi, J.-R.; Montgomery, W. D.; Cha, J. K. J. Am. Chem. Soc., 1989, 111, 2580–2582.

(o) Pearson, W. H.; Lin, K.-C. Tetrahedron Lett., 1990, 31, 7571.

(p) Miller, S. A.; Chamberlin, A. R. J. Am. Chem. Soc., 1990, 112, 8100–8112.

(q) Ikota, N.; Hanaki, A. Chem. Pharm. Bull. 1990, 38, 2712.

(r) Fleet, G. W. J. U.S. Pat. No. 5,023,340, 1991.

(s) Naruse, M.; Aoyagi, S.; Kibayashi, C. J. Org. Chem., 1994, 59, 1358–1364.

(t) Hunt, J. A.; Roush, W. R. Tetrahedron Lett. 1995, 36, 501–504.

(u) Kang, S. H.; Kim, G. T. Tetrahedron Lett. 1995, 36, 5049–5052.

For a synthesis of the non-natural (+)-enantiomer of swainsonine, see:

(v) Oishi, T.; Iwakuma, T.; Hirama, M.; Ito, S. Synlett 1995, 404–406.

For formal syntheses, see:

(w) Gonzalez, F. B.; Barba, A. L.; Espina, M. R. Bull. Chem. Soc. Jpn. 1992, 65, 567–574.

(x) Honda, T.; Hoshi, M.; Kanai, K.; Tsubuki, M. J. Chem. Soc., Perkin Trans. 1 1994, 2091–2101.

(y) Angermann, J.; Homann, K.; Reissig, H.-U.; Zimmer, R. Synlett 1995, 1014–1016.

(z) Zhou, W.-S.; Xie, W.-G.; Lu, Z.-H.; Pan, X.-F. Tetrahedron Lett., 1995, 36, 1291–1294.

(aa) Zhou, W.-S.; Xie, W.-G.; Lu, Z.-H.; Pan, X.-F. J. Chem. Soc., Perkin Trans. 1 1995, 2599–2604.

However, there is still a need for a practical synthesis of this important alkaloid. Perhaps the most practical routes developed to date are those reported by the research groups of Fleet (see: Carpenter, N. M.; Fleet, G. W. J.; diBello, I. C.; Winchester, B.; Fellows, L. E.; Nash, R. J. Tetrahedron Lett. 1989, 30, 7261–7264; and Fleet, G. W. J. U.S. Pat. No. 5,023,340, 1991) and Cha (see: Bennett, R. B., III; Choi, J.-R.; Montgomery, W. D.; Cha, J. K. J. Am. Chem. Soc., 1989, 111, 2580–2582). In addition, a short synthetic route recently developed has not proven amenable to scale-up (Pearson, W. H.; Lin, K.-C. Tetrahedron Lett., 1990, 31, 7571).

Thus, there remains a need for a synthesis of (–)-swainsonine that is relatively short and efficient and uses simple reactions that allow good reproducibility and material throughput. There also remains a need for intermediates useful for the production of swainsonine.

SUMMARY OF THE INVENTION

Accordingly, it is one object of the present invention to provide a novel method for producing swainsonine.

It is another object of the present invention to provide a novel method for producing (–)-swainsonine.

It is another object of the present invention to provide a novel method for producing (–)-swainsonine which is convenient and economical and affords (–)-swainsonine in high yields.

It is another object of the present invention to provide novel intermediates useful for producing swainsonine.

It is another object of the present invention to provide novel intermediates useful for producing (–)-swainsonine.

These and other objects, which will become apparent during the following detailed description, have been achieved by the inventors' discovery that:

(i) reacting a compound of formula (8):

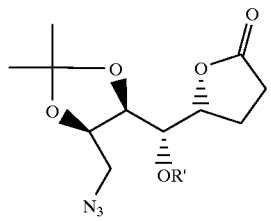

(8)

in which R' is methanesulfonyl, trifluoromethanesulfonyl, or toluenesulfonyl, preferably methanesulfonyl with $H_2$ in the presence of $Pd(OH)_2$ followed by NaOMe, to obtain a compound of the formula (9):

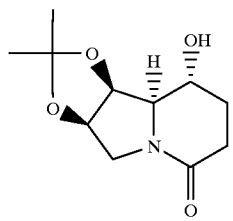

(9)

and (ii) reducing the carbonyl group and hydrolyzing the ketal group in the compound of formula (9) affords (–)-swainsonine of formula (1):

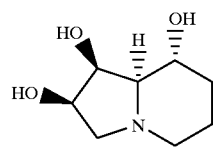

(1)

The present invention has also been achieved by the inventors' discovery of the following novel intermediates useful for producing (–)-swainsonine:

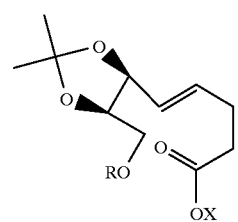

(4)

in which R is selected from the group consisting of trimethylsilyl, triethylsilyl, tri-isopropylsilyl, diphenyl-tert-butylsilyl and tert-butyldimethysilyl, preferably tert-butyldimethylsilyl, and X is $C_{1-4}$-alkyl;

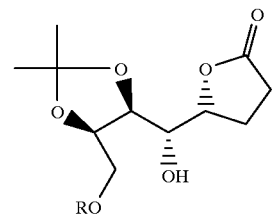

(5a)

in which R is selected from the group consisting of trimethylsilyl, triethylsilyl, tri-isopropylsilyl, diphenyl-tert-butylsilyl and tert-butyldimethysilyl, preferably tert-butyldimethylsilyl;

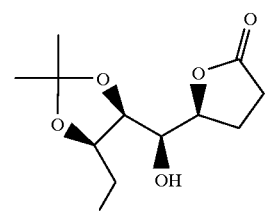

(5b)

in which R is selected from the group consisting of trimethylsilyl, triethylsilyl, tri-isopropylsilyl, diphenyl-tert-butylsilyl and tert-butyldimethysilyl, preferably tert-butyldimethylsilyl; and (6)

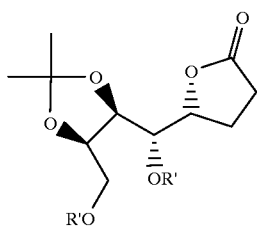

in which R' is selected from the group consisting of hydrogen, methanesulfonyl, trifluoromethanesulfonyl, and toluenesulfonyl, preferably hydrogen or methanesulfonyl.

DETAILED DESCRIPTION OF THE PREFERRED EMBODIMENTS

Thus in a first embodiment, the present invention provides a novel, convenient, and economical synthesis of (−)-swainsonine, using the strategy shown in scheme 1.

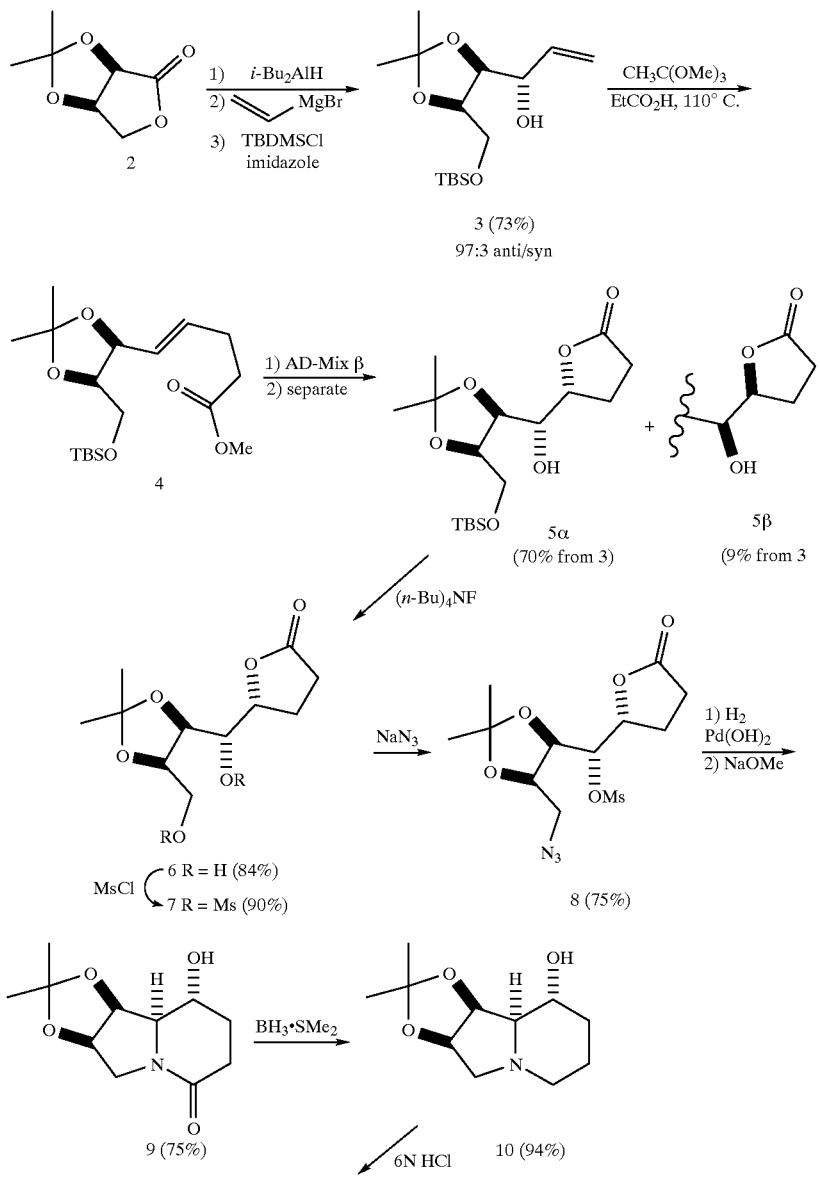

-continued

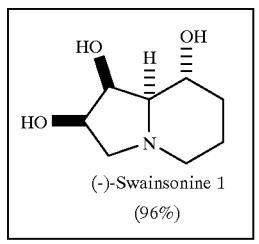

(-)-Swainsonine 1
(96%)

The reductive double-cyclization of an azide bearing two remote electrophilic centers for the synthesis of other bioactive alkaloids and their analogs has previously been used for the synthesis of:

A. Slaframine:
Pearson, W. H.; Bergmeier, S. C. J. Org. Chem. 1991, 56, 1976–1978.
Pearson, W. H.; Bergmeier, S. C.; Williams, J. P. J. Org. Chem. 1992, 57, 3977–3987.

B. Australine and alexine stereoisomers:
Pearson, W. H.; Hines, J. V. Tetrahedron Lett. 1991, 32, 5513–5516.

C. Ring-expanded analogs of swainsonine:
Pearson, W. H.; Hembre, E. J. Tetrahedron Lett. 1993, 34, 8221–8224.
Pearson, W. H.; Hembre, E. J. J. Org. Chem., 1996, 61, 5537–5545.

D. Ring-expanded analogs of australine and alexine:
Pearson, W. H.; Hembre, E. J. J. Org. Chem., 1996, 61, 5546–5556.

For related one-pot double cyclizations using azido epoxides or amino epoxides, see: Setoi, H., et al J. Org. Chem. 1985, 50, 3948–3950; Carpenter, N. M., et al Tetrahedron Lett. 1989, 30, 7261–7264; Kim, Y. G.; Cha, J. K. Tetrahedron Lett. 1989, 30, 5721–5724; Ina, H.; Kibayashi, C. J. Org. Chem., 1993, 58, 52–61; Jirousek, M. R.; Cheung, A. W.-H.; Babine, R. E.; Sass, P. M.; Schow, S. R.; Wick, M. M. Tetrahedron Lett., 1993, 34, 3671–3674; Kim, N.-S.; Choi, J.-R.; Cha, J. K. J. Org. Chem 1993, 58, 7096–7099; Poitout, L.; Le Merrer, Y.; Depezay, J.-C. Tetrahedron Lett., 1994, 35, 3293–3296; and Lohray, B. B.; Jayamma, Y. and Chatterjee, M. J. Org. Chem 1995, 60, 5958–5960.

The synthesis of swainsonine (Scheme 1) may begin with 2,3-O-isopropylidene-D-erythronolactone (2), which is commercially available (Aldrich) or may be prepared in large quantities from inexpensive D-isoascorbic acid (see: Cohen, N.; Banner, B. L.; Laurenzano, A. J.; Carozza, L. In Organic Syntheses, Collective Vol. IV; J. P. Freeman, Ed.; Wiley: N.Y., 1990; pp 297–301; and Dunigan, J.; Weigel, L. O. J. Org. Chem. 1991, 56, 6225–6227). Reduction of (2) with diisobutylaluminum hydride (see: Cohen, N., et al J. Am. Chem. Soc. 1983, 105, 3661–3672) provided 2,3,-O-isopropylidene-D-erythrose. Addition of vinylmagnesium bromide (see: Mekki, B.; et al Tetrahedron Lett. 1991, 32, 5143–5146) followed by selective monoprotection of the resulting diol afforded the allylic alcohol (3) (97:3 anti/syn) in 73% yield from (2).

Separation of the diastereomeric mixture was possible, however it was unnecessary, since both allylic alcohols (3) produce the same g,d-unsaturated ester (4) when subjected to Johnson orthoester Claisen rearrangement conditions (see: Johnson, W. S.; et al J. Am. Chem. Soc. 1970, 92, 741–743). The rearrangement produced only the E-isomer within the limits of detection by high-field $^1$H-NMR.

Without purification, (4) was submitted to the Sharpless dihydroxylation procedure (see: Sharpless, K. B.; et al J. Org. Chem. 1992, 57, 2768–2771; Wang, Z.-M.; et al Tetrahedron Lett. 1992, 33, 6407–6410; and Keinan, E.; et al Tetrahedron Lett. 1992, 33, 6411–6414) affording the lactones (5a) and (5b) in 70% and 9% yields, respectively, after separation. Alternatively, Cha's method may be used to transform (4) into swainsonine. Cha and coworkers made a compound similar to (4) (ethyl ester, Z-alkene, free hydroxy instead of t-butyldimethylsilyloxy) by a Wittig route.

Removal of the silyl protecting group from (5a) gave the diol (6), which was smoothly converted to the crystalline dimesylate (7). Selective displacement of the less hindered mesylate of (7) with sodium azide afforded (8). Palladium-catalyzed hydrogenolysis of (8) to the amine followed by filtration of the catalyst and treatment of the filtrate with sodium methoxide caused cyclization to the known crystalline bicyclic lactam (9) in 75% yield. Reduction of (9) with borane-methyl sulfide complex gave a 94% yield of crystalline compound (10), also a known compound (see Setoi, H.; et al J. Org. Chem. 1985, 50, 3948–3950; Bashyal, B. P.; et al Tetrahedron 1987, 43, 3083; Bennett, R. B.; et al J. Am. Chem. Soc. 1989, 111, 2580–2582; and Naruse, M.; et al J. Org. Chem. 1994, 59, 1358–1364) which was hydrolyzed to swainsonine (1) in 96% yield. While the reduction of (9) to (10) has been reported by Fleet using $BH_3 \cdot Me_2S$ (see: Carpenter, N. M.; et al Tetrahedron Lett. 1989, 30, 7261–7264) their procedure involves isolation of the borane complex of (10). The present procedure is adapted from a similar one by Keck which was used to make an epimer of swainsonine, see: Keck, G. E.; Romer, D. R. J. Org. Chem. 1993, 58, 6083–6089. While not the shortest synthesis, this route involves simple, reproducible steps that work well on a substantial scale. Using this method, 4.5 g of swainsonine was be prepared in 20% overall yield from the lactone (2), requiring 11 steps involving three chromatographic separations and five crystallizations.

To summarize, a simple route to the clinically useful anticancer agent (-)-swainsonine (1) has been developed. Given the current scarcity and high cost of this material, this preparation will be useful to researchers in this area.

Other features of the invention will become apparent in the course of the following descriptions of exemplary embodiments which are given for illustration of the invention and are not intended to be limiting thereof.

EXAMPLES

General methods

All commercial reagents (if liquid) were distilled prior to use. All other solid reagents were used as obtained. Tetrahydrofuran was distilled from sodium/benzophenone ketyl. Toluene, dichloromethane, dimethyl sulfoxide, and triethylamine were distilled from calcium hydride. Dimethylformamide was distilled from barium oxide at reduced pressure. Methanol and ethanol were distilled from calcium oxide. All reactions were conducted under an atmosphere of dry nitrogen. Analytical thin layer chromatography (tlc) was conducted on precoated silica gel plates (Kieselgel 60 F254, 0.25 mm thickness, manufactured by E. Merck & Co., Germany). For visualization, tlc plates were either stained with iodine vapor or phosphomolybdic acid solution. Flash column chromatography was performed according to the general procedure described by Still (see: Still, W. C.; et al J. Org. Chem. 1978, 43, 2923–2925) using flash grade Merck Silica Gel 60 (230–400 mesh). Gas chromatographic (GC) analyses were performed using a 530 m methylpolysiloxane column (3 m film thickness, 5 m length) using flame ionization detection. A standard temperature program of 100° C. for 2 min followed by a 40° C./min ramp to 200° C. was used. Elemental analyses were performed by the University of Michigan Department of Chemistry CHN / AA Services Branch. High resolution mass spectrometric (HRMS) measurements are accurate to within 2.2 ppm (electron impact, EI), 3.9 ppm (chemical ionization, CI), or 3.3 ppm (fast-atom bombardment, FAB), based on measurement of the performance of the mass spectrometer on a standard organic sample.

EXAMPLE 1

(3S,4S,5R)-6-tert-Butyldimethylsilyloxy-4,5-O-isopropylidenedioxy-1-hexen-3-ol (3).

The reduction of 2,3-O-isopropylidene-D-erythronolactone (2) was performed using a modified version of Cohen's procedure (see: Cohen, N.; et al J. Am. Chem. Soc. 1983, 105, 3661–3672). Diisobutylaluminum hydride (101 mL of a 1.5 M soln. in toluene, 152 mmol) was added in a dropwise fashion via an addition funnel to a cold (−78° C.) solution of 2,3-O-isopropylidene-D-erythronolactone (2) (see: Cohen, N.; et al in Organic Synthesis, Collective Vol, IV; J. P. Freeman, Ed.; Wiley, N.Y., 1990; pp 297–301) (20.0 g, 126 mmol) in $CH_2Cl_2$ (360 mL). After 2 h, methanol (20 mL) was added, followed by brine (10 mL). After warming to room temperature, the mixture was diluted with ether (500 mL) and $MgSO_4$ (150 g) was added. After stirring vigorously for 4 h, the mixture was filtered with suction through a sintered glass funnel, and the filter cake was washed with ether (100 mL). The filtrate was concentrated to give 17.0 g (84%) of crude 2,3 -O-isopropylidene-D-erythrose as a pale yellow oil that was used without further purification.

The addition of vinylmagnesium bromide to 2,3-O-isopropylidene-D-erythrose was carried out according to Mekki et al (see: Mekki, B.; Singh, G.; Wightman, R. H. Tetrahedron Lett. 1991, 32, 5143–5146). Since the communication by Mekki, et. al does not provide experimental procedures or spectroscopic data, we have chosen to include these details herein. The crude lactol was dissolved in THF (380 ml), cooled to −78° C., and vinylmagnesium bromide (315 ml of a 1 M soln in THF, 315 mmol) was added in a dropwise fashion via an addition funnel. The mixture was then warmed to 0° C. After 6 h, the reaction was quenched by the addition of saturated aqueous $NH_4Cl$ (100 mL). The resulting mixture was diluted with water (200 mL) and extracted with EtOAc (3×200 mL). The combined organic layers were washed with brine, dried ($MgSO_4$), filtered, and concentrated to give 19.5 g of a yellow oil that was used without further purification. Purification of a small sample by chromatography (3:1 to 2:1 hexane/EtOAc gradient) provided an analytically pure sample of the pure anti-diol, (2R,3S,4S)-2,3-O-isopropylidene-1,2,3,4-tetrahydroxy-5-hexene: Rf=0.14 (3:1 hexane/EtOAc); bp 94–100° C. at 0.25 mmHg; [α]23D −42.5°(c 1.53, $CHCl_3$); $^1H$ NMR (300 MHz, $CDCl_3$) d 5.99 (ddd, J=5.6, 10.6, 17.3 Hz, 1H), 5.38 (dt, J=1.4, 17.3 Hz, 1H), 5.27 (dt, J=1.4, 10.5 Hz, 1H), 4.3 (m, 2H), 4.05 (dd, J=5.8, 8.4 Hz, 1H), 4.02 (m, 1H), 3.8 (m, 3H), 1.43 (s, 3H), 1.35 (s, 3H); $^{13}C$ NMR (75 MHz, $CDCl_3$) d 137.5, 116.5, 108.4, 79.6, 77.3, 70.6, 60.7, 27.7, 25.3:IR (neat) 3383 (s), 2987 (s), 2937 (m), 1456 (w), 1382 (m), 1220 (s), 1048 (s); MS (CI, $CH_4$) m/z (rel intensity) 189 [(M+H)+, 40], 173 (22), 131 (80), 113 (100); HRMS (CI, $CH_4$) calcd for $C_9H_{16}O_4H$ [(M+H)+] 189.1127, found 189.1122; Anal calcd for $C_9H_{16}O_4$: C, 57.43; H, 8.57; found C, 57.44; H, 8.60.

The crude diol mixture was dissolved in THF/DMF (3:1, 400 mL). The solution was cooled to 0° C. and tert-butyldimethylsilyl chloride (18.8 g, 125 mmol) and imidazole (17.6 g, 259 mmol) were added. After 45 min, the mixture was poured into ether (400 mL) and the organic layer was washed with 1M HCl (2×200 mL). The combined aqueous layers were back-extracted with ether (2×100 mL). The combined organic layers were washed with water, 5% $NaHCO_3$, and brine, then dried ($MgSO_4$), filtered, and concentrated. Chromatography (100:1 to 20:1 hex/EtOAc gradient) provided 27.1 g (71% from (2) of the anti-allylic alcohol (3) followed by 0.88 g (2% from (2) of the syn-allylic alcohol diastereomer. Data for 3-anti Rf=0.48 (6:1 hexane/EtOAc); [α]23D −36.3°(c 0.58, $CHCl_3$); $^1H$ NMR ($CDCl_3$, 300 MHz) d 6.02 (ddd, J=5.2, 10.6, 17.2 Hz, 1H), 5.44 (dt, J=1.6, 17.2 Hz, 1H), 5.25 (dt, J=1.6, 10.6 Hz, 1H), 4.3-4.2 (m, 2H), 4.19 (d, J=3.2 Hz, 1H), 4.06 (dd, J=5.5, 9.2 Hz, 1H), 3.86 (dd, J=9.9, 10.5 Hz, 1H), 3.65 (dd, J=3.5, 10.5 Hz, 1H), 1.39 (s, 3H), 1.34 (s, 3H), 0.92 (s, 9H), 0.14 (s, 6H); $^{13}C$ NMR ($CDCl_3$, 75 MHz) d 137.4, 115.7, 108.5, 80.6, 77.2, 69.8, 62.0, 28.0, 25.8, 25.3, 18.3, −5.47, −5.52; IR (neat) 3470 (br m), 2933 (s), 2885 (s), 2859 (s), 1472 (m), 1380 (m), 1077 (s) $cm^{-1}$; MS (CI, $NH_3$) m/z (rel intensity) 303 [(M+H)+, 18], 285 (9), 262 (19), 245 (100), 227 (42), 173 (46); HRMS (CI, $NH_3$) calcd for $C_{15}H_{30}O_4SiH$ [(M+H)+] 303.1992, found 303.1984; Anal. calcd for $C_{15}H_{30}O_4Si$: C, 59.56; H, 10.00; found C, 59.29; H, 10.00.

Data for minor isomer (3-syn): Rf=0.41 (6:1 hex/EtOAc); [α]23D −3.9°(c 1.05, $CHCl_3$); 1H NMR ($CDCl_3$, 360 MHz) d 6.01 (ddd, J=5.2, 10.6, 17.2 Hz, 1H), 5.40 (dt, J=1.7, 17.2 Hz, 1H), 5.22 (dt, J=1.6, 10.6 Hz, 1H), 4.37 (m, 1H), 4.21 (td, J=4.4, 6.7 Hz, 1H), 4.13 (dd, J=4.0, 6.5 Hz, 1H), 3.96 (dd, J=7.0, 10.7 Hz, 1H), 3.76 (dd, J=4.4, 10.7 Hz, 1H), 3.01 (d, J=5.8 Hz, 1H), 1.49 (s, 3H), 1.37 (s, 3H), 0.91 (s, 9H), 0.10 (s, 6H); $^{13}C$ NMR ($CDCl_3$, 90 MHz) d 137.7, 115.8, 108.2, 79.6, 77.3, 67.0, 61.7, 27.2, 25.8, 24.9, 18.3, −5.6; IR (neat) 3475 (br, m) 2931 (s), 1858 (s), 1472 (m), 1381 (m) $cm^{-1}$; MS (CI, $NH_3$) m/z (rel intensity) 303 [(M+H)+, 1.5], 287 (6), 245 (100), 227 (26), 117 (41); HRMS (CI, $NH_3$) calcd for $C_{15}H_{30}O_4SiH$ [(M+H)+] 303.1992, found 303.1983; Anal. calcd for $C_{15}H_{30}O_4Si$: C, 59.56; H, 10.00; found C, 59.61; H, 10.01.

EXAMPLE 2

Methyl (E)-(6S,7R)-8-tert-butyldimethylsilyloxy-6,7-O-isopropylidenedioxy-4-octenoate (4).

Trimethyl orthoacetate (77 mL, 640 mmol) and propionic acid (1.9 mL, 26 mmol) were added to a solution of the allylic alcohol (3) (27.9 g, 92.3 mmol) in toluene (500 mL). The flask was fitted with a distillation head and the mixture was heated at reflux, distilling off methanol as it formed. GC was used to monitor the disappearance of starting material (tR=4.0 min) and the appearance of product (tR=5.2 min, see General methods above for GC conditions). After 24 h, the mixture was cooled to room temperature and concentrated to give 32.7 g (99%) of the title compound (4) as a pale yellow oil that was used without further purification. Purification of a small sample by chromatography (10:1 hex/EtOAc) provided an analytically pure sample. Rf=0.40 (6:1 hex/EtOAc); [α]23D −0.9°(c 1.08, CHCl$_3$); $^1$H NMR (CDCl$_3$, 360 MHz) d 5.77 (m, 1H), 5.57 (dd, J=7.7, 15.4 Hz, 1H), 4.58 (t, J=7.1 Hz, 1H), 4.15 (dd, J=6.1, 12.2 Hz, 1H), 3.68 (s, 3H), 3.59 (m, 2H), 2.41 (m, 4H), 1.46 (s, 3H), 1.36 (s, 3H), 0.89 (s, 9H), 0.06 (s, 6H); $^{13}$C NMR (CDCl$_3$, 90 MHz) d 173.3, 132.8, 126.5, 108.3, 78.6, 78.3, 62.3, 51.6, 33.4, 27.9, 27.6, 25.8, 25.4, 18.2, −5.4; IR (neat) 2930 (s), 2857 (m), 1743 (s), 1438 (m), 1375 (m) cm$^{-1}$; MS (CI, NH$_3$) m/Z (rel intensity) 376 [(M+NH$_4$)+, 12], 318 (87), 301 (100), 271 (29), 186 (32), 169 (29), 151 (28); HRMS (CI, NH$_3$) calcd for C$_{18}$H$_{34}$O$_5$SiNH$_4$ [(M+NH$_4$)+] 376.2519, found 376.2519; Anal. calcd for C$_{18}$H$_{34}$O$_5$Si: C, 60.30; H, 9.56; found: C, 60.12; H 9.61.

EXAMPLE 3

(5R)-5-[(1'S,2'R,3'R)-(4'-tert-Butyldimethylsilyloxy)-1'-hydroxy-2',3'-O-isopropylidenedioxybutyl]tetrahydrofuran-2-one (5a) and (5S)-5-[(1'R,2'R,3'R)-(4'-tert-Butyldimethylsilyloxy)-1'-hydroxy-2',3'-O-isopropylidenedioxybutyl]tetra-hydrofuran-2-one (5b).

The dihydroxylation was performed using the general procedure reported by Sharpless (see: Sharpless, K. B.; Amberg, W.; Bennani, Y. L.; Crispino, G. A.; Hartung, J.; Jeong, K.-S.; Kwong, H.-L.; Morikawa, K.; Wang, Z.-M.; Xu, D.; Zhang, X.-L. J. Org. Chem. 1992, 57, 2768–2771). A solution of the crude alkene (4) (32.0 g, 89.2 mmol) in t-BuOH (150 mL) was added to a cold (0° C.), mechanically stirred, biphasic mixture of water (475 mL) and t-butanol (300 mL) containing potassium ferricyanide (93 g, 280 mmol), potassium carbonate (39 g, 280 mmol), potassium osmate dihydrate (0.35 g, 0.95 mmol), (DHQD)2-PHAL (0.75 g, 0.96 mmol), (see Sharpless, K. B.; et al J. Org. Chem. 1992, 57, 2768–2771), and methanesulfonamide (9.0 g, 94.5 mmol). The solution was allowed to warm slowly to room temperature. GC was used to monitor the disappearance of the alkene (4) (tR=5.2 min) and the appearance of the product (tR=6.8 min, see General methods above for GC conditions). After 18 h, sodium sulfite (150 g) was added, and the mixture was stirred an additional 1 h. EtOAc (400 mL) was then added, the layers were separated, and the aqueous layer was extracted with EtOAc (3×400 mL). The combined organic layers were washed with 2N KOH (400 mL), then dried (MgSO$_4$) and concentrated. Chromatography (10:1 to 3:1 hex/EtOAc gradient) provided 22.6 g (70% from (3)) of (5a) as a colorless oil followed by 2.98 g (9% from (3) of (5b) as a colorless oil. Data for (5a): Rf=0.28 (3:1 hex/EtOAc); [α]23D −36.3° (c 0.58, CHCl$_3$); $^1$H NMR (CDCl$_3$, 360 MHz) d 4.84 (ddt, J=1.4, 5.7, 7.2 Hz, 1H), 4.42 (dd, J=5.6, 9.7 Hz, 1H), 4.26 (ddd, J=3.6, 5.6, 9.9 Hz, 1H), 4.14 (br d, J=3.3 Hz, 1H), 3.77 (m, 2H), 3.65 (dd, J=3.5, 10.5 Hz, 1H), 2.72 (m, 1H), 2.44 (m, 1H), 2.32 (m, 2H), 1.37 (s, 3H), 1.35 (s, 3H), 0.91 (s, 9H), 0.13 (s, 6H); $^{13}$C NMR (CDCl$_3$, 90 MHz) d 178.0, 108.7, 79.1, 76.6, 76.4, 71.0, 61.8, 28.4, 27.9, 25.7, 25.3, 23.8, 18.2, −5.6, −5.7; IR (neat) 3430 (br w), 2934 (m) , 2858 (m) , 1778 (s), 1472 (w), 1370 (m) cm$^{-1}$; MS (CI, NH$^3$) m/z (rel intensity) 378 [(M+NH$_4$)+, 52], 361 [(M+H)+, 100], 170 (27), 153 (27); HRMS (CI, CH$_4$) calcd for C$_{17}$H$_{32}$O$_6$SiH [(M+H)+] 361.2046, found 361.2035; Anal. calc. for C$_{17}$H$_{32}$O$_6$Si: C, 56.64; H, 8.95; found C, 56.58; H, 9.04.

Data for (5b): Rf=0.18 (3:1 hex/EtOAc); [α]23D +4.5° (c 0.95, CHC$_{13}$); $^1$H NMR (CDCl$_3$, 300 MHz) d 4.77 (td, J=2.9, 6.6 Hz, 1H), 4.31 (t, J=6.0 Hz, 1H), 4.18 (ddd, J=3.6, 5.8, 8.5 Hz, 1H), 3.94 (ddd, J=3.0, 4.1, 6.0 Hz, 1H), 3.83 (dd, J=8.5, 10.7 Hz, 1H), 3.66 (dd, J=3.6, 10.7 Hz, 1H), 2.85 (d, J=4.2 Hz, 1H), 2.69 (m, 1H), 2.46 (m, 1H), 2.28 (m, 2H), 1.45 (s, 3H), 1.36 (s, 3H), 0.89 (s, 9H), 0.08 (s, 6H); $^{13}$C NMR (CDCl$_3$, 75 MHz) 177.3, 108.4, 79.8, 77.2, 76.8, 70.6, 61.6, 28.2, 27.6, 25.8, 25.3, 24.1, 18.3, −5.4; IR (neat) 3470 (br, m), 2954 (m), 2858 (m), 1778 (s), 1463 (m), 1381 (m) cm$^{-1}$; MS (CI, NH$_3$) m/z (rel intensity) 378 [(M+NH$_4$)+, 100], 361 [(M+H)+, 31], 320 (20), 303, (20), 170 (18), 153 (23); HRMS (CI, NH$_3$ and CH$_4$) calcd for C$_{17}$H$_{32}$O$_6$SiH [(M+H)+] 361.2046, found 361.2033; Anal. calcd. for C$_{17}$H$_{32}$O$_6$Si: C, 56.64; H, 8.95; found C, 56.27; H, 8.91.

EXAMPLE 4

(5R)-5-[(1'S,2'R,3'R)-1',4'-Dihydroxy-2',3'-O-isopropylidenedioxybutyl]tetrahydrofuran-2-one (6).

A solution of tetra-n-butylammonium fluoride (19.8 g of a 75% w/w solution in water, 56.7 mmol) in THF (50 mL) was added to a cold (0° C.) solution of (5a) (18.6 g, 51.6 mmol) in THF (250 mL). After 1.5 h, silica gel (25 g) and water (10 mL) were added, and the mixture was stirred another 10 min. The mixture was then filtered through Celite, rinsing with ether (300 mL). The filtrate was dried (MgSO$_4$) and concentrated. Chromatography (30:60:1 to 30:60:10 hex/EtOAc/EtOH gradient) provided 11.7 g (84%) of the diol (6) as a pale yellow oil. Rf=0.25 (20:1 CHCl$_3$/MeOH); [α]23D −66.9° (c 0.90, CHCl$_3$); $^1$H NMR (CDCl$_3$, 360 MHz) d 4.87 (m, 1H), 4.33 (m, 2H), 4.22 (d, J=6.3 Hz, 1H), 3.8 (m, 3 H), 3.38 (t, J=5.7 Hz, 1H), 2.68 (ddd, J=7.2, 9.3, 17.5 Hz, 1H), 2.50 (ddd, J=7.3, 10.0, 17.5 Hz, 1H), 2.33 (m, 2H), 1.41 (s, 3H), 1.36 (s, 3H); $^{13}$C NMR (CDCl$_3$, 90 MHz) d 178.5, 108.6, 80.0, 76.8, 76.2, 70.8, 60.7, 28.6, 27.8, 25.2, 23.6; IR (neat) 3390 (br, s), 2987 (s), 2939 (s), 1770 (s), 1372 (s) cm$^{-1}$; MS (CI, NH$_3$) m/z (rel intensity) 264 [(M+NH$_4$)+, 100], 247 [(M+H)+, 55], 229 (15), 206 (15), 160 (11); HRMS (CI, NH$_3$) calcd for C$_{11}$H$_{18}$O$_6$H [(M+H)+] 247.1182, found 247.1187; Anal. calcd. for C$_{11}$H$_{18}$O$_6$: C, 53.65; H, 7.37; found C, 53.44; H, 7.33.

EXAMPLE 5

(5R)-5-[(1'S,2'R,3'R)-1',4'-Bis(methanesulfonyloxy)-2',3'-O-isopropylidenedioxybutyl]tetrahydrofuran-2-one (7).

Methanesulfonyl chloride (10.1 mL, 130 mmol) was added to a cold (0° C.) solution of the diol (6) (10.7 g, 43.3 mmol) and DMAP (0.265 g, 2.16 mmol) in pyridine (130 mL). The mixture was stirred for 30 min and then placed in a refrigerator (2 ° C.). After 16 h, ethyl acetate (400 mL) was added, and the solution was washed with 10% HCl (3×100 mL). The aqueous layers were back extracted with ethyl acetate (100 mL). The combined organic layers were washed with sat. NaHCO$_3$ and brine, then dried (MgSO$_4$), and concentrated to give a foamy yellow solid. Recrystallization from EtOAc/hex (~1:1) provided 15.7 g (90%) of the dimesylate (7) as a pale yellow crystalline solid in three crops. Rf=0.11 (1:1 hex/EtOAc); mp 120–123° C.; [α]23D +39.8° (c 1.31, CHCl$_3$); $^1$H NMR (CDCl$_3$, 300 MHz) d 4.81 (ddd, J=2.9, 5.9, 7.7 Hz, 1H), 4.52 (td, J=3.1, 6.4 Hz, 1H), 4.46 (dd, J=3.1, 10.8 Hz, 1H), 4.40 (dd, J=4.8, 5.8, 1H), 4.32 (dd, J=6.6, 10.8 Hz, 1H), 3.25 (s, 3H), 3.08 (s, 3H), 2.74 (m, 1H), 2.58 (m, 1H), 2.44 (m, 2H), 1.54 (s, 3H), 1.40 (s, 3H); $^{13}$C NMR (CDCl$_3$,90 MHz) d 175.9, 109.4, 78.8, 77.9, 76.1, 75.1, 69.3, 39.2, 37.3, 27.4, 27.3, 25.6, 23.9; IR (neat) 3027 (w), 2989 (m), 2942 (m), 1784 (s), 1462 (w), 1359 (s) cm-$^{-1}$; MS (CI, NH$_3$) m/z (rel intensity) 420 [(M+NH$_4$)+, 100], 403 [(M+H)+, 2], 246 (56); HRMS (CI, NH$_3$) calcd for $C_{13}H_{22}O_{10}S_2NH_4$ [(M+NH$_4$)+] 420.0998, found 420.0998; Anal calcd for $C_{13}H_{22}O_{10}S_2$: C, 38.80, H, 5.51; found C, 38.93; H, 5.63.

EXAMPLE 6

(5R)-5-[(1'S,2'R,3'R)-4'-Azido-2',3'-O-isopropylidenedioxy-1'-methanesulfonyloxybutyl]tetrahydrofuran-2-one (8).

Sodium azide (12.1 g, 187 mmol) was added to a solution of the dimesylate (7) (15.0 g, 37.4 mmol) in DMSO (110 mL), and the flask was heated at 80° C. (oil bath). After 36 h, the solution was cooled and poured into water (300 mL) and extracted with EtOAc (3×200 mL). The combined organic extracts were washed with brine, then dried (MgSO$_4$), and concentrated. Crystallization from CHCl$_3$/Et$_2$O provided 8.50 g (65%) of the azido-mesylate (8) as a white crystalline solid in two crops. The mother liquor was concentrated, and chromatography (2:1 hex/EtOAc to 50:50:1 hex/EtOAc/EtOH gradient) provided 0.99 g (9%) of the diazide [Rf=0.62 (1:1 hex/EtOAc)], followed by an additional 1.33 g of (8) [total yield 9.83 g (75%)], and 0.75 g (5%) of recovered starting dimesylate (7). Data for (8): Rf=0.33 (1:1 hex/EtOAc); [α]23D +75.0° (c 0.52, CHCl$_3$); mp 136° C.; $^1$H NMR (CDCl$_3$, 300 MHz) d 5.01 (dd, J=3.8, 6.0 Hz, 1H), 4.81 (ddd, J=3.7, 6.1, 7.8 Hz, 1H), 4.43 (ddd, J=3.5, 5.9, 7.2 Hz, 1H), 4.35 (t, J=5.7 Hz, 1H), 3.53 (dd, J=3.5, 13.1 Hz, 1H), 3.47 (dd, J=7.2, 13.1 Hz, 1H), 3.22 (s, 3H), 2.69 (m, 1H), 2.56 (dd, J=7.1, 9.8 Hz, 1H), 2.3-2.5 (m, 2H), 1.54 (s, 3H), 1.40 (s, 3H); $^{13}$C NMR (CDCl$_3$, 90 MHz) d 175.8, 109.2, 78.8, 78.1, 76.6, 75.8, 51.6, 39.2, 27.6, 27.5, 25.4, 24.2; IR (neat) 2990 (m), 2940 (m), 2105 (s), 1784 (s), 1360 (s) cm$^{-1}$; MS (CI, NH$_3$) m/z (rel intensity) 367 [(M+NH$_4$)+, 100], 322 (16), 228 (24); HRMS (CI, NH$_3$) calcd. for $C_{12}H_{19}N_3O_7SNH_4$ [(M+NH$_4$)+] 367.1287, found 367.1288; Anal. calcd. for $C_{12}H_{19}N_3O_7S$: C, 41.26; H, 5.48; N, 12.03; found C, 40.97; H, 5.36; N, 11.98.

EXAMPLE 7

(1S,2R,8R,8aR)-8-Hydroxy-1,2-O-isopropylidenedioxy-indolizidin-5-one (9).

Palladium hydroxide on carbon (1.50 g) was added to a solution of the azido mesylate (8) (9.75 g, 27.9 mmol) in MeOH (500 mL). The flask was evacuated by aspirator and purged with hydrogen three times, and the resulting heterogeneous mixture was stirred under a balloon of hydrogen. After 6 h, the hydrogen was evacuated and the mixture was filtered through Celite, rinsing with MeOH (100 mL). Sodium methoxide (3.20 g, 59.3 mmol) was added, and the solution was warmed to reflux. The reaction was monitored by IR for the disappearance of the lactone carbonyl stretch at 1784 cm$^{-1}$ and appearance of the lactam carbonyl stretch at 1625 cm$^{-1}$. After 60 h, the solution was cooled to room temperature and concentrated to a volume of ca. 50 mL, causing precipitation of a white solid. The mixture was diluted with CH$_2$Cl$_2$ (500 mL), florisil (50 g) was added, and the mixture was stirred at room temperature for 30 min. The suspension was then filtered through Celite, and the filtrate was concentrated to give a yellow oil that crystallized upon standing. Recrystallization from EtOAc/ether (1:2) provided 3.85 g (61%) of lactam (9) as a white crystalline solid. The mother liquor was concentrated to give a yellow oil that was purified by chromatography (10% EtOH/EtOAc) to give another 0.91 g of crystalline (9) [total yield: 4.76 g (75%)]. Rf=0.38 (10:1 CHCl$_3$/MeOH); mp 129° C. (lit 126–128° C., 125–127° C.); [α]23D +12.6° (c 1.06, MeOH), [lit. [α]25D +4.30 (c 0.16, MEOH); 1H NMR (300 MHz, CDCl$_3$) d 4.81 (dd, J=4.5, 6.0 Hz, 1H), 4.75 (t, J=5.5 Hz, 1H), 4.19 (d, J=13.5 Hz, 1H), 4.15 (ddd, J=4.2, 8.4, 15.5 Hz, 1H), 3.33 (dd, J=4.5, 13.6 Hz, 1H), 2.69 (d, J=4.5 Hz, 1H), 2.53 (ddd, J=2.9, 6.6, 18.0 Hz, 1H), 2.41 (ddd, J=6.4, 11.7, 18.0 Hz, 1H), 2.13 (m, 1H), 1.87 (m, 1H), 1.43 (s, 3H), 1.34 (s, 3H); $^{13}$C NMR (CDCl$_3$, 75 MHz) d 168.2, 112.1, 79.8, 77.6, 77.2, 66.3, 65.4, 50.6, 29.8, 26.4, 24.7; IR (neat) 3361 (br m), 2987 (m), 2938 (m), 2870 (m), 1625 (s), 1471 (m), 1454 (m) cm$^{-1}$; MS (EI, 70 eV) m/z (rel intensity) 227 (M+, 58), 212 (53), 152 (51), 85 (100), 68 (53), 43 (76); HRMS calcd for $C_{11}H_{17}NO_4$ (M+) 227.1157, found 227.1159. These data are consistent with literature values (see: Setoi, H.; Takeno, H.; Hashimoto, M. J. Org. Chem. 1985, 50, 3948–3950).

EXAMPLE 8

(1S,2R,8R,8aR)-8-Hydroxy-1,2-O-isopropylidenedioxy-indolizidine (10).

Borane-methyl sulfide complex (59 mL of a 2 M solution in THF, 118 mmol) was added over a period of 30 min via an addition funnel to a cooled (0° C.) solution of the lactam (9) (6.65 g, 29.3 mmol) in THF (725 mL). After 30 min, the solution was warmed to room temperature. After another 2 h, the reaction was quenched by the slow addition of ethanol (440 mL, caution: hydrogen evolution) and concentrated to give a viscous oil which was redissolved in EtOH (700 mL) and heated at reflux for 2 h. After cooling to room temperature, the solution was concentrated to give 6.6 g of a colorless, crystalline solid which was recrystallized from 200 mL of hot hexanes to provide 5.87 g (94%) of the title compound, Rf=0.41 (10:1 CHCl$_3$/MeOH); mp 101–103° C. (lit mp 104–106° C., 106–108° C., 100–103° C., 101–104° C.); [α]23D −81.7° (c 1.10, MeOH), [lit [α]25D −73.3° (c 0.35, MeOH), [α]20D −65.8° (c 0.5, MeOH), [α]25D −67.3° (c 0.46, MeOH), [α]25D −72.76 (c 0.43, MeOH)] $^1$H NMR (300 MHz, CDCl$_3$) d 4.70 (dd, J=4.6, 6.2 Hz, 1H), 4.61 (dd, J=4.2, 6.3 Hz, 1H), 3.83 (m, 1H), 3.15 (d, J=10.7 Hz, 1H), 2.99 (dt, J=3.0, 10.4 Hz, 1H), 2.33 (br s, 1H), 2.12 (dd, J=4.2, 10.7 Hz, 1H), 2.05 (m, 1H), 1.85 (m, 1H), 1.6–1.7 (m, 3H), 1.51 (s, 3H), 1.34 (s, 3H), 1.2–1.3 (m, 1H); $^{13}$C NMR (90 MHz, CDCl$_3$) d 111.3, 79.1, 78.2, 73.6, 67.3, 59.8, 51.6, 32.9, 25.9, 24.7, 24.0; IR (neat) 3198 (br m), 2980 (m), 2941 (s), 2857 (w), 2792 (m), 1466 (w), 1446 (w), 1371 (m) cm$^{-1}$; MS (EI, 70eV) m/z (rel intensity) 213 (M+, 53), 198 (24), 138 (100), 113 (82), 96 (712), 43 (41); HRMS calcd for $C_{11}H_{19}NO_3$ (M+) 213.1365, found 213.1367. These data are consistent with those reported in the literature (see: Bennett, R. B., III; Choi, J.-R.; Montgomery, W. D.; Cha, J. K. J. Am. Chem. Soc., 1989, 111, 2580–2582).

EXAMPLE 9

(1S, 2R, 8R, 8aR)-1,2,8-Trihydroxyindolizidine [(−)-Swainsonine] (1).

Prepared according to the published procedure. A solution of 10 (5.75 g, 27 mmol) in THF (27 mL) was treated with 6N HCl (27 mL) at room temperature for 12 h. The solution was then concentrated, the residue was applied to an ion exchange column (Dowex 1×8 200 OH—, 30 g), which was eluted with water. The fractions containing (1) were identified by TLC (iodine stain). These fractions were concentrated to give a white crystalline solid which was recrystallized from CHCl$_3$/MeOH/ether to give 4.50 g (96%) of swainsonine (1) in three crops. Rf=0.35 (3:1 CHCl$_3$/MeOH w/1% NH$_4$OH); mp 139–142° C. (lit mp 141–143° C., 144–145° C., 140–142° C.); [α]23D −74.0° (c 0.98, MeOH) [lit [α]25D −82.6° (c 1.03, MeOH), [α]25D −73.8° (c 0.21, EtOH), [α]25D −75.7° (c 2.33, MeOH)]; $^1$H NMR (300

MHz, D$_2$O) d 4.39 (ddd, J=2.8, 5.9, 8.0 Hz, 1H), 4.29 (dd, J=3.5, 5.8 Hz, 1H), 3.84 (app td, J=4.6, 10.3 Hz, 1H), 3.0 (m, 1H), 2.97 (dd, J=2.8, 11.3 Hz, 1H), 2.70 (dd, J=8.1, 11.3 Hz, 1H), 2.04–2.15 (m, 3H), 1.76 (m, 1H), 1.55 (qt, J=4.1, 13.2 Hz, 1H), 1.28 (qd, J=4.5, 12.3 Hz, 1H); $^{13}$C NMR (90 MHz, D$_2$O, MeOH internal standard) d 72.6, 69.4, 68.9, 66.0, 60.3, 51.6, 32.2, 22.9; IR (neat) 3366 (br s), 2944 (s), 2884 (m), 2804 (m), 2727 (m), 1660 (w), 1378 (m) cm-1; MS (EI, 70 eV) m/z (rel intensity) 173 (M+, 16), 155 (30), 113 (73), 96 (73), 83 (100); HRMS calcd for C$_8$H$_{15}$NO$_3$ (M+) 173.1052, found 173.1052. These data are consistent with those reported in the literature (see: Bennett, R. B., III; Choi, J.-R.; Montgomery, W. D.; Cha, J. K. J. Am. Chem. Soc., 1989, 111, 2580–2582).

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A compound of the formula (4):

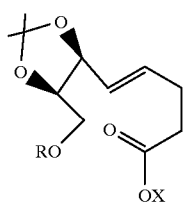

(4)

wherein R is selected from the group consisting of trimethylsilyl, triethylsilyl, tri-isopropylsilyl, diphenyl-tert-butylsilyl, and tert-butyldimethylsilyl and X is C$_{1-4}$-alkyl.

2. The compound of claim 1, wherein R is tert-butyldimethylsilyl.

3. A compound of the formula (5a) or (5b):

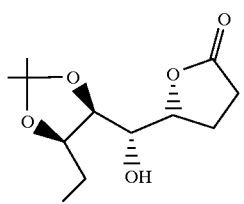

(5a)

(5b)

wherein R is selected from the group consisting of trimethylsilyl, triethylsilyl, tri-isopropylsilyl, diphenyl-tert-butylsilyl and tert-butyldimethylsilyl.

4. The compound of claim 3, wherein R is tert-butyldimethylsilyl.

5. A compound of the formula (6):

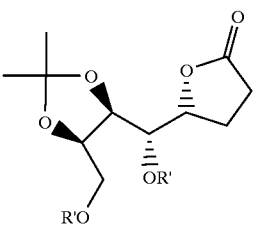

(6)

wherein R' is selected from the group consisting of hydrogen, methanesulfonyl, trifluoromethanesulfonyl, and toluenesulfonyl.

6. The compound of claim 5, wherein R' is hydrogen or methanesulfonyl.

7. A compound of the formula (8):

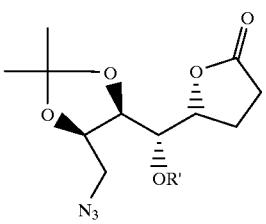

(8)

wherein R' is selected from the group consisting of methanesulfonyl, trifluoromethanesulfonyl, and toluenesulfonyl.

8. The compound of claim 7, wherein R' is methanesulfonyl.

9. A method for preparing (−)-swainsonine, comprising:
(i) reacting a compound of formula (8):

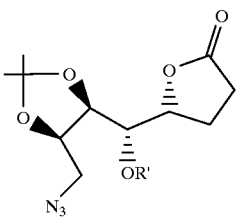

(8)

wherein R' is selected from the group consisting of methanesulfonyl, trifluoromethanesulfonyl, and toluenesulfonyl, with H$_2$ in the presence of Pd(OH)$_2$ followed by NaOMe, to obtain a compound of formula (9):

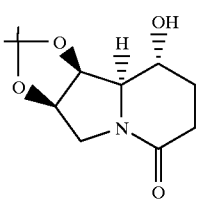

(9)

and (ii) reducing the carbonyl group and hydrolyzing the ketal group in the compound of formula (9) to obtain (−)-swainsonine of formula (1):

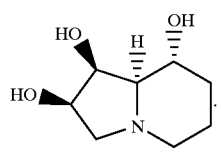
(1)

10. The method of claim 9, wherein R' is methanesulfonyl.

11. The method of claim 9, wherein said compound of formula (8) is prepared by reacting a compound of formula (7)

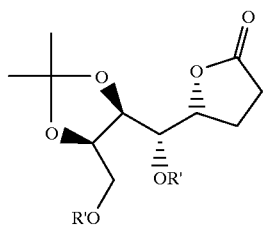
(7)

wherein R' is selected from methanesulfonyl, trifluoromethanesulfonyl, and toluenesulfonyl, with $NaN_3$.

12. The method of claim 11, wherein R' is methanesulfonyl.

13. The method of claim 11, wherein said compound of formula (7) is prepared by reacting a compound of formula (6)

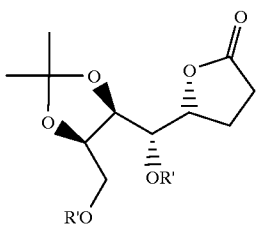
(6)

wherein R' is hydrogen, with a compound selected from the group consisting of methanesulfonyl chloride, trifluoromethanesulfonyl chloride, and toluenesulfonyl chloride.

14. The method of claim 13, wherein said compound of formula (6) is prepared by reacting a compound of formula (5a)

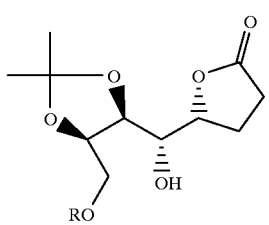
(5a)

with $(n\text{-Bu})_4NF$.

* * * * *